United States Patent
Welzig et al.

(10) Patent No.: US 9,629,932 B2
(45) Date of Patent: *Apr. 25, 2017

(54) PHOTODYNAMIC DIAGNOSIS, FORMULATIONS USABLE AS PHOTOSENSITIZERS FOR THIS PURPOSE, METHOD FOR THE PRODUCTION AND USE THEREOF

(71) Applicant: Sanochemia Pharmazeutika AG, Vienna (AT)

(72) Inventors: Stefan Welzig, Vienna (AT); Beate Kalz, Steinbrunn (AT); Jozsef Gungl, Agfalva (HU); Klaus Gerdes, Dusseldorf (DE); Werner Frantsits, Vienna (AT); Christina Abrahamsberg, Vienna (AT)

(73) Assignee: SANOCHEMIA PHARMAZEUTIKA AG, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/878,573

(22) Filed: Oct. 8, 2015

(65) Prior Publication Data

US 2017/0087256 A1 Mar. 30, 2017

(30) Foreign Application Priority Data

Sep. 28, 2015 (AT) ..................... 629/2015

(51) Int. Cl.
*A61K 9/00* (2006.01)
*A61K 49/00* (2006.01)

(52) U.S. Cl.
CPC ...... *A61K 49/0054* (2013.01); *A61K 49/0021* (2013.01)

(58) Field of Classification Search
CPC .................................. A61K 49/0054
See application file for complete search history.

(56) References Cited

U.S. PATENT DOCUMENTS 6,472,439 B1  10/2002  Schierstedt
7,390,510 B2   6/2008  Kubin et al.

FOREIGN PATENT DOCUMENTS

DE        19756677        6/1999
DE        102014204138    9/2015
EP        1289562         3/2003
WO        2015131891      9/2015
WO        WO 2015/131891  * 11/2015

OTHER PUBLICATIONS

Machine translation of WO 2015/131891, Aug. 2016.*
Austrian Search Report dated Apr. 12, 2016; Application No. A 629/2015.
A. Huygens et al., "Stability of different formulations and ion pairs of hypericin", European Journal of Pharmaceutics and Biopharmaceutics, Apr. 2005, vol. 59, No. 3, pp. 461-464.

* cited by examiner

*Primary Examiner* — Paul Dickinson
(74) *Attorney, Agent, or Firm* — Young & Thompson

(57) ABSTRACT

In the early detection of cancer, in particular bladder cancer, a photodynamic diagnosis uses, as a photosensitizer, a formulation that contains sodium hypericinate that is bonded to polyvinylpyrrolidone or complexed with polyvinylpyrrolidone.

6 Claims, No Drawings

PHOTODYNAMIC DIAGNOSIS, FORMULATIONS USABLE AS PHOTOSENSITIZERS FOR THIS PURPOSE, METHOD FOR THE PRODUCTION AND USE THEREOF

FIELD OF THE INVENTION

The invention relates to a method for photodynamic diagnosis, a new formulation of hypericin, a method for the production of the formulation, and the use thereof for the production of a photosensitizer.

BACKGROUND OF THE INVENTION

Bladder cancer is the most common cancer of the urinary tract. Bladder cancer affects men more than three times more frequently than women. It is the seventh most commonly diagnosed type of cancer in men (Ferlay et al., 2013). Approximately 75-85% of patients with newly-diagnosed bladder cancer show non-muscle-invasive bladder tumors, i.e., tumors that are limited to the mucous membrane. In this case, the tumor stages are carcinoma in situ (Tis), Ta, or T1 (Babjuk et al., 2015). The rates of recurrence in the case of non-muscle-invasive bladder carcinoma are very high. The probability of recurrence is approximately 15 to 61% within the first year and 31 to 78% after 5 years (Witjes, Douglass, 2007). The high rates of recurrence require a year-long monitoring and follow-up of once-diseased patients.

The most common symptom of non-muscle-invasive bladder cancer is hematuria. In addition, irritating symptoms or pains in the lower urinary tract can also occur. A physical study does not provide any information about a potential non-muscle-invasive bladder tumor (Babjuk et al., 2015). The visual inspection of the bladder with an endoscope and white-light illumination (white-light cystoscopy) and a removal of tissue samples represents a first diagnosis. This method is reliable for exophytic tumors. Flat carcinomas (in particular Tis), dysplasia, multifocal growth, and microscopic lesions are very much more difficult to detect and are often overlooked during white-light cystoscopy.

The method of fluorescence cystoscopy (also referred to as photodynamic diagnosis (PDD)) improves the detection rates of non-muscle-invasive bladder cancer, in particular of Tis, and thus reduces the recurrence rate (Burger et al., 2013; Kausch et al., 2010; Stenzel et al., 2010).

The photodynamic diagnosis (PDD) uses the photoactive properties of certain compounds, so-called photosensitizers, which preferably accumulate in tumor tissue and improve the optical delineation between normal and neoplastic tissue.

The basic principle of the photodynamic diagnosis (PDD) is based on a two-step method, comprising a systemic or topical application of a photosensitizer, and the activation of the photosensitizer by irradiation with visible light with a suitable wavelength.

The "gold standard" in the detection of non-muscle-invasive bladder cancer is white-light cystoscopy. Upon suspicion of Tis, however, the use of fluorescence cystoscopy is recommended (Babjuk et al., 2015), by which on average 20% more Tis can be found (Witjes et al., 2010).

The porphyrin precursor 5-aminolevulinic acid (5-ALA) and the derivative hexaminolevulinic acid (HAL) are used in fluorescence diagnosis. Both substances are pro-drugs. By metabolizing the pro-drug, a photoactive molecule is produced, which is used for PDD. The only substance approved as a pharmaceutical agent for PDD in the indication of bladder carcinoma is hexaminolevulinic acid (Hexvix®, Cysview®).

The properties of hypericin (1,3,4,6,8,13-hexahydroxy-10,11-dimethylphenanthro (1,10,9,8-opqra) perylene-7,14-dione) as a photosensitizer and indicator for cancer cells, especially for detection of non-muscle-invasive tumors of the urothelium, are known. Hypericin is not a pro-drug and must not be metabolized in the tissue, but rather can be stimulated directly with light with a suitable wavelength, as soon as the hypericin has accumulated in the tissue.

However, pure hypericin is hydrophobic and water-insoluble. For this reason, in the past in preclinical studies, a water-soluble polymer, polyethylene glycol (PEG), or in clinical studies, serum proteins were used as effective hypericin transporters/carriers in order to bring the insoluble hypericin into the target cells (D'Hallewin et al., 2000 and 2002; Olivo et al., 2003; Pytel et al., 2002).

The solubility of hypericin can be increased by the presence of the adjuvant polyvinylpyrrolidone ("povidone," PVP) (WO 01/89576 A2).

A formulation that consists of 25 mg of PVP and 0.25 mg of hypericin was clinically studied in 57 patients (Kubin et al., 2008). With respect to flat lesions (Tis and dysplasia), a detection rate of 100% for Tis and 85% for dysplasia was achieved on the lesion level with PVP-hypericin-supported PDD, while only 33% (Tis) and 31% (dysplasia) were detected under white-light cystoscopy.

The improved detection on the lesion level is also evident on the patient level: in the case of 16% of the patients, the PVP-hypericin detects supported PDD lesions that were overlooked in white-light cystoscopy. The instillation time (dwell time in the bladder) of the PVP-hypericin solution was approximately 60-220 minutes (on average, 111±39 (SD) minutes) (Kubin et al., 2008).

Even when the known PDD study has achieved good results, a serious problem remains unsolved. The long instillation time (i.e., the retaining of the administered solution in the patient's bladder) of at least 60 minutes represents a burden for patients with non-muscle-invasive bladder carcinoma, who very often suffer from pains or cramps.

SUMMARY OF THE INVENTION

As a first object, the invention is based on making available an improved method for photodynamic diagnosis. This object is achieved with a method for photodynamic diagnosis of tumors, whereby a complex or a compound that consists of hypericin and a polymeric complexing agent is used, in which as a photosensitizer, a complex or a compound that consists of an alkali salt of hypericin and a polymeric complexing agent is used.

The object of the invention is also to make available a sterile pharmaceutical formulation of hypericin, which can be produced on an industrial scale and has a corresponding long-term stability. This formulation of hypericin is supposed to be easier to use than known formulations of hypericin as a diagnostic agent for bladder cancer.

This object is achieved with a formulation of hypericin that contains hypericin that is bonded or complexed to a polymeric complexing agent, whereby hypericin is present as a salt.

The object of the invention is also to make available a method for the production of a formulation of hypericin that can be used in photodynamic therapy as a photosensitizer.

This object is achieved with a method in which hypericin salt is bonded or complexed to a polyethylene glycol or to a poly-N-vinyl amide, preferably polyvinylpyrrolidone (PVP).

Moreover, the invention is based on an advantageous use of the formulation according to the invention.

In this respect, the invention relates to the use of the formulation according to the invention for the production of a photosensitizer that can be used in photophysical or photodynamic diagnosis and for early detection of cancer.

Preferred and advantageous embodiments of the therapy according to the invention, the formulation according to the invention, the method for the production, and the use thereof are subjects of the subclaims.

DETAILED DESCRIPTION OF THE INVENTION

Surprisingly enough, it has been shown that the formulation of hypericin according to the invention can be applied successfully in a stable manner and thus under clinical conditions in photodynamic diagnosis only when hypericin is present as a salt.

Within the framework of a clinical study, it has been shown that the formulation of hypericin according to the invention is especially well-suited for the detection of malignant lesions in patients under suspicion of non-muscle-invasive bladder carcinoma. Moreover, the formulation of hypericin according to the invention makes possible, without having an adverse effect on the results of the PDD, considerably shorter installation times, which means an advantageous reduction of the burden of the patients.

Surprisingly enough, an application of the formulation according to the invention with a dose of 22.5 mg of PVP and 0.225 mg of hypericin in combination with an instillation time of 30 to at most 50 minutes for a PDD of the non-muscle-invasive bladder carcinoma has proven to be an optimal dose.

In the diagnosis according to the invention, in particular using the formulation according to the invention, Tis lesions, which had been overlooked with white-light cystoscopy, were identified at an instillation time of 30 to 50 minutes in 35% of the patients.

A complete removal of the tumor (resection) represents the first important step for the treatment of patients. Often, a complete resection of the tumor tissue is difficult. This has the result that tumor material is overlooked and remains in the patient's bladder. For this reason, it is especially important to detect and to remove the edges and boundaries of the tumor tissue completely.

The application of the diagnosis according to the invention, in particular with the formulation according to the invention with a hypericin content of 0.225 mg (Example 1), showed a better recognizability of the tissue detail, especially with respect to the edge areas of the tumors. As a result, discrimination between malignant and benign tissue is facilitated, and the tumor can be removed completely.

This better differentiation between malignant and benign tissue is also to be achieved with a hypericin content of 0.500 mg and an instillation time of only 15 minutes.

Since Tis lesions are associated with extremely high rates of recurrence and a very high probability of progression (i.e., the development of a tumor into a further advanced stage or the occurrence of metastases), an improved detection rate and thus a complete removal of the tumor using the formulation of hypericin according to the invention represent a significant advantage relative to the further course of the disease.

The instillation time of 15, on average 30 to at most 50, minutes that is necessary in the diagnosis according to the invention, in particular when using the formulation according to the invention, is considerably shorter than any instillation time that is used for a PDD with hexaminolevulinic acid. As soon as after an instillation time of on average 30 minutes, malignant lesions could be diagnosed using the above-mentioned hypericin formulation. This significantly shortened instillation time represents a great relief for patients with non-muscle-invasive bladder carcinoma and increases the probability of remaining within the necessary exposure time.

Below, examples of the formulation of hypericin according to the invention are described:

General procedure for producing a formulation with the active ingredient sodium hypericinate:

The goal is the production of a hypericin-containing formulation for application as a photosensitizer in the area of the photodynamic diagnosis.

The formulation according to the invention is produced from a salt of hypericin, in particular from Na-hypericinate.

In order to define the hypericin content of the starting material, in addition to the determination of contents, primarily water content and, in the case of sodium hypericinate, the proportion of sodium are specified.

The chemical-physical properties can have an influence on the formulation of the pharmaceutical agent.

For clinical application, a stability of the formulation according to the invention is necessary. The stability is ensured by the composition of the finished product and at the same time also relates to the production method. Because of the buffer systems used, adequate stability of the bulk solution can also be achieved during production until lyophilization of the finished product takes place.

As buffer systems, various additives can be used, which preferably both for the bulk solution and for the reconstituted solution achieve a physiologically compatible pH and an osmotic pressure of 290 mOsmol/kg after reconstitution with 50 ml of water for injection. Phosphate or citrate buffer systems can be used primarily.

After the bulk solution is made up from the above-mentioned components, the corresponding amount of the bulk solution is decanted into injection flasks and freeze-dried.

Example 1

From Na-hypericinate, a solution with a target weighed-in amount of 27.0 mg of hypericin is produced.

5.0 g of the hypericin solution is added to 562.5 mg of PVP k25 and completely dissolved.

This solution is quantitatively made up to 250.0 g with a phosphate buffer solution. The final concentration of this solution is 0.0225 mg of hypericin/g of solution.

For the lyophilization, a defined amount of the thus obtained bulk solution is decanted into injection flasks, and the finished lyophilizate is produced with a corresponding lyo program.

Example 2

The procedure is the same as indicated in Example 1, whereby instead of PVP k25, PVP k17 is used for complexing Na-hypericinate.

Example 3

The procedure is the same as indicated in Example 1, whereby instead of PVP k25, PVP k30 is used for complexing Na-hypericinate.

Example 4

The procedure is the same as indicated in Examples 1, 2, or 3, whereby instead of the phosphate buffer solution, a citric acid buffer solution is used.

The bulk solutions that are produced as described in Examples 1 to 4 can be produced with different hypericin contents.

From the hypericin stock solution (produced from sodium hypericinate), the following dilutions can be produced before further treatment:

A defined amount of solvent is added to and homogenized in 0.4 g of the hypericin solution mentioned in Example 1. In this case, in the next step, only 187.5 mg of PVP (different types of PVP are possible) is added for complexing. In the finished bulk solution, a final concentration of 0.0075 mg of hypericin/g of solution is thus reached.

A defined amount of solvent is added to and homogenized in 0.2 g of the hypericin solution mentioned in Example 1. In this case, in the next step, only 62.5 mg of PVP (different types of PVP are possible) is added thereto for complexing. In the finished bulk solution, a final concentration of 0.0025 mg of hypericin/g of solution is thus reached.

In a clinical study, the formulation of hypericin according to Example 1 was instilled at a dose of 22.5 mg of PVP and 0.225 mg of hypericin for a time period of, on average, 30 to 35 minutes, at most up to 50 minutes, in the patients' bladders. Then, a cystoscopy was performed, first under white light and then under fluorescent light. Suspicious lesions were removed and classified by means of histological examination.

In a total of 20 patients, Tis lesions could be detected and histologically confirmed. The PDD using a formulation of hypericin according to the invention in this case shows a decisive advantage in the detection of Tis in 35% of patients. Without PDD that uses the formulation of hypericin according to the invention, the Tis lesions remained undiscovered in these patients.

REFERENCES

Babjuk, M.; Böhle, A.; Burger, M.; Compérat, E.; Kaasinen, E.; Palou, J.; Rouprêt, M.; van Rhijn, B. W. G.; Shariat, S.; Sylvester, S.; and Zigeuner, R. European Association of Urology Guidelines, 2015 Edition: Guidelines on Non-Muscle-Invasive Bladder Cancer (Ta, T1 and CIS)

Burger, M.; Grossman, H. B.; Droller, M.; Schmidbauer, J.; Hermann, G.; Dr. Goescu, O.; Ray, E.; Fradet, Y.; Karl, A.; Burgués, J. P.; Witjes, J. A.; Stenzl, A.; Jichlinski, P.; Jocham, D. Photodynamic Diagnosis of Non-Muscle-Invasive Bladder Cancer with Hexaminolevulinate Cystoscopy: A Meta-Analysis of Detection and Recurrence Based on Raw Data. Eur Urol. 2013 November; 64 (5): 846-854

D'Hallewin, M. A.; de Witte, P. A.; Waelkens, E.; Merlevede, W.; Baert, L. Fluorescence Detection of Flat Bladder Carcinoma In Situ After Intravesical Instillation of Hypericin. J. Urol. 2000; 164(2): 349-351

D'Hallewin, M. A.; Kamuhabwa, A. R.; Roskams, T.; de Witte, P. A. M.; Baert, L. Hypericin-Based Fluorescence Diagnosis of Bladder Carcinoma. BJU International 2002; 89: 760-763

D'Hallewin, M. A.; Bezdetnaya, L.; Guillemin, F. Fluorescence Detection of Bladder Cancer: A Review. Eur Urol. 2002; 42(5): 417-425

Ferlay, J.; Steliarova-Foucher, E.; Lortet-Tieulent, J.; Rosso, S.; Coebergh, J. W.; Comber, H.; Forman, D.; Bray, F. Cancer Incidence and Mortality Patterns in Europe: Estimates for 40 Countries in 2012. Eur J Cancer. 2013 April; 49(6): 1374-1403

Kausch, I.; Sommerauer, M.; Montorsi, F., et al.: Photodynamic Diagnosis in Non-Muscle-Invasive Bladder Cancer: A Systematic Review and Cumulative Analysis of Prospective Studies. Eur Urol. April 2010; 57(4): 595-606

Kubin, A.; Meissner, P.; Wierrani, F.; Burner, U.; Bodenteich, A.; Pytel, A.; Schmeller, N. Fluorescence Diagnosis of Bladder Cancer with New Water Soluble Hypericin Bound to Polyvinylpyrrolidone: PVP-Hypericin. Photochem Photobiol. 2008; 84(6): 1560-1563

Olivo, M.; Lau, W.; Manivasager, V.; Tan, P. H.; Soo, K. C.; Cheng, C. Macro-microscopic Fluorescence of Human Bladder Cancer Using Hypericin Fluorescence Cystoscopy and Laser Confocal Microscopy. Int J Oncol 2003; 23(4): 983-990

Pytel, A.; Schmeller, N. New Aspect of Photodynamic Diagnosis of Bladder Tumors: Fluorescence Cytology. Urology 2002; 59: 216-219

Stenzl, A.; Burger, M.; Fradet, Y.; Mynderse, L. A.; Soloway, M. S.; Witjes, J. A.; Kriegmair, M.; Karl, A.; Shen, Y.; Grossman, H. B. Hexaminolevulinate Guided Fluorescence Cystoscopy Reduces Recurrence in Patients with Nonmuscle Invasive Bladder Cancer. J Urol. November 2010; 184(5): 1907-1913

Witjes, J. A.; Douglass, J. The Role of Hexaminolevulinate Fluorescence Cystoscopy in Bladder Cancer. Nat Clin Pract Urol. 2007 October; 4(10): 542-549

Witjes, J. A.; Redorta, J. P.; Jacqmin, D.; Sofras, F.; Malmström, P. U.; Riedl, C.; Jocham, D.; Conti, G.; Montorsi, F.; Arentsen, H. C.; Zaak, D.; Mostafid, A. H.; Babjuk, M. Hexaminolevulinate-Guided Fluorescence Cystoscopy in the Diagnosis and Follow-Up of Patients with Non-Muscle-Invasive Bladder Cancer: Review of the Evidence and Recommendations. Eur Urol. 2010 April; 57(4): 607-614

The invention claimed is:

1. A method for photodynamic diagnosis of tumors, comprising:
photosensitizing with a photosensitizer that is a stable complex or a stable compound of a sodium or potassium salt of hypericin and a polymeric complexing agent selected from the group consisting of polyethylene glycol and poly-N-vinyl amide, the photosensitizer containing 0.225 mg of hypericin
wherein the photosensitizer is obtained from a lyophilizate obtained from a solution of the sodium or potassium metal salt of hypericin, the polymeric complexing agent and a buffer system comprising a phosphate buffer or a citric acid buffer.

2. The method according to claim 1, wherein a photodynamic diagnosis for early detection of cancer is made.

3. The method according to claim 1, wherein the poly-N-vinyl amide is a polyvinylpyrrolidone (PVP) of various degrees of polymerization and cross-linking.

4. The method according to claim 3, wherein the polyvinylpyrrolidone is PVP k17, PVP k25 or PVP k30.

5. The method according to claim 1, wherein a photodynamic diagnosis for detection of bladder cancer, is made.

6. The method according to claim 1, further comprising the following successive steps:
 a) preparing the solution of the sodium or potassium salt of hypericin;
 b) dissolving the complexing agent in the solution;
 c) adding sufficient of the buffer system to obtain a concentration of 0.0225 mg hypericin/g solution; and
 d) lyophilizing the solution to obtain the lyophilizate to obtain the photosensitizer containing the 0.225 mg hypericin.

* * * * *

UNITED STATES PATENT AND TRADEMARK OFFICE
CERTIFICATE OF CORRECTION

PATENT NO. : 9,629,932 B2
APPLICATION NO. : 14/878573
DATED : *April 25, 2017
INVENTOR(S) : Stefan Welzig et al.

It is certified that error appears in the above-identified patent and that said Letters Patent is hereby corrected as shown below:

On the Title Page

Amend Item (72) to read as follows:
--(72) Inventors: Stefan Welzig, Vienna (AT); Beate Kaelz, Steinbrunn (AT); Jozsef Gungl, Agfalva (HU); Klaus Gerdes, Dusseldorf (DE); Werner Frantsits, Vienna (AT); Christina Abrahamsberg, Vienna (AT)--.

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*